(12) United States Patent
Jo et al.

(10) Patent No.: US 8,685,113 B2
(45) Date of Patent: Apr. 1, 2014

(54) FOAM TYPE HAIR DYING AGENT COMPOSITION

(75) Inventors: Bong-Lim Jo, Gyeonggi-do (KR); Hye-Jin Moon, Seoul (KR)

(73) Assignee: Dong Sung Pharm. Co., Ltd., Seoul (KR)

( * ) Notice: Subject to any disclaimer, the term of this patent is extended or adjusted under 35 U.S.C. 154(b) by 0 days.

(21) Appl. No.: 13/699,717

(22) PCT Filed: Aug. 30, 2011

(86) PCT No.: PCT/KR2011/006402
§ 371 (c)(1),
(2), (4) Date: Nov. 24, 2012

(87) PCT Pub. No.: WO2012/144698
PCT Pub. Date: Oct. 26, 2012

(65) Prior Publication Data
US 2014/0026332 A1    Jan. 30, 2014

(30) Foreign Application Priority Data

Apr. 22, 2011    (KR) .................... 10-2011-0037879

(51) Int. Cl.
*A61Q 5/10*    (2006.01)
(52) U.S. Cl.
USPC ............... 8/405; 8/406; 8/435; 8/477; 8/561; 8/580; 8/611; 8/617

(58) Field of Classification Search
USPC ............ 8/405, 406, 435, 477, 561, 580, 611, 8/617
See application file for complete search history.

(56) References Cited

U.S. PATENT DOCUMENTS

| 7,651,533 B2 | 1/2010 | Legrand | |
| 2002/0184717 A9* | 12/2002 | Cottard et al. | 8/405 |

FOREIGN PATENT DOCUMENTS

| JP | 2002-308736 A | 10/2002 |
| JP | 2004-189634 A | 7/2004 |
| KR | 10-1987-0000352 | 8/1987 |
| KR | 10-2004-0049819 A | 6/2004 |

* cited by examiner

*Primary Examiner* — Eisa Elhilo
(74) *Attorney, Agent, or Firm* — Frommer Lawrence & Haug LLP; Ronald R. Santucci (57) ABSTRACT

Disclosed is a first composition of an oxidative permanent hair dye product that includes a $C_1$-$C_4$ alcohol, an anionic surfactant, a nonionic surfactant, an antioxidant, an oxidative dye, a $C_{14}$-$C_{22}$ fatty alcohol, a metal sequestering agent, an alkali agent, and purified water. According to the oxidative permanent hair dye product according to the present invention, foams generated by mixing a liquid first composition that includes a dye and a liquid second composition that includes an oxidant continuously retained on hair for more than 30 minutes, and thus hair, even close to the root, can be simply and conveniently colored in the same manner as shampooing without using a comb or brush.

14 Claims, 3 Drawing Sheets

FOAM TYPE HAIR DYING AGENT COMPOSITION

This application is a 371 of PCT/KR2011/006402 filed on Aug. 30, 2011 published on Oct. 26, 2012 under publication number WO 2012/144698 A which claims priority benefits to Korean Patent Application Number 10-2011-0037879 filed Apr. 22, 2011 the entire disclosure of which is incorporated herein by reference.

BACKGROUND (a) Technical Field

The present inventions relates to a foam-type oxidative permanent hair dye composition.

(b) Background Art

Hair dye products are classified into three types, temporary hair dye products, long lasting hair dye products, and permanent hair dye products according to the degree of fastness of a dye on hair.

A permanent hair dye product according to the present invention is an oxidative permanent hair dye product which includes a first composition that includes an oxidative dye and a second composition that includes an oxidant. The permanent hair dye product has been widely used due to its long lasting color compared to those of conventional hair dye products. The oxidative permanent hair dye product includes powders, liquids, gels, creams, etc.

As a hair dye product in its infancy, a powdered oxidative permanent hair dye product, includes a first composition that includes an oxidative dye and an aqueous polymer such as sodium carboxymethyl cellulose and hydroxyethyl cellulose for improving viscosity, and a second composition that includes 3.0 to 12.0 wt % of an oxidant, in which the first composition and the second composition are mixed upon using. However, the powdered oxidative permanent hair dye product needs to be stirred for 5 to 20 minutes until the aqueous polymer in the form of powder is hydrated to have a viscosity suitable for a dyeing procedure.

A liquid oxidative permanent hair dye product includes a first composition and a second composition, both of which are in liquid forms, in which the first composition includes a dye and an aqueous polymer dissolved in water with a surfactant for increasing viscosity. Thus, there is no need to wait for use of the product as in the powdered hair dye products, and the mixture of the first and second compositions may be used immediately after mixing. However, the viscosity of the liquid oxidative permanent hair dye product is not sufficient so that the product can flow down when applied to short hair and contaminate skin or clothes.

A creamy oxidative permanent hair dye product, one of the recently developed oxidative permanent hair dye products, is an emulsion obtained by mixing a dye, a water phase such as an alkali agent and purified water, and an oil phase such as a higher alcohol and a fatty acid by using an emulsifier. The creamy hair dye product is efficiently applied to hair due to soft creamy property and does not flow down due to high viscosity, so that it is the most popular product.

However, since the creamy oxidative permanent hair dye product should be applied to hair by using a comb or brush, parts of hair to which the hair dye product is not applied are not dyed, and thus an elaborate skill is required. Particularly, it is very difficult for a user to apply the product to long hair at the back of the head or thick hair alone, it is difficult for unskilled helper to uniformly apply the product, and it takes a long time for about 5 to 20 minutes to apply the product to hair. In addition, the principle of dyeing hair by mixing the first and second compositions of the oxidative permanent hair dye product is that oxidation of the dye of the first composition occurs by oxygen generated by the oxidant of the second composition, and the oxidized dye colors hair. As the reaction time between the first composition and the second composition increases, the hair dye effect is improved. Thus, if the product is applied to hair for more than 5 minutes for elaborate application, the brightness of hair applied in the early stage is different from that of hair applied in the last stage so that hair cannot be uniformly dyed and the hair may be spotted. Further, long hair to which a hair dye product is applied cannot be fixed at the head but flows down due to the weight of a large amount of hair dye product, so as to contaminate clothes and surroundings. In order to prevent such contamination, the hair needs to be fixed by using tongs or hairpins while dyeing hair.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The present invention has been made in an effort to solve the above-described problems associated with prior art.

An object of the present invention is to provide a convenient oxidative permanent hair dye product that is easily applied to hair compared to cream-type or gel-type oxidative permanent hair dye products that is applied by using a comb and brush since foams of the hair dye product generated by mixing first and second compositions are applied to hair in the same manner as shampooing, that is uniformly dyed without spots since time for the application is reduced, and that does not cause long hair to flow down due to the weight of the applied hair dye product since light and highly adhesive foams are generated.

Another object of the present invention is to provide a hair dye product, foams of which are continuously retained for more than 30 minutes after being applied to hair in order to prevent contamination of skin or clothes caused when foams applied to the hair turn to liquid and flow down.

In an aspect, the present invention provides a first composition of an oxidative permanent hair dye product including a $C_1$-$C_4$ alcohol, an anionic surfactant, a nonionic surfactant, an antioxidant, an oxidative dye, a $C_{14}$-$C_{22}$ fatty alcohol, a metal sequestering agent, an alkali agent, and purified water.

In another aspect, the present invention provides an oxidative permanent hair dye product including the first composition of an oxidative permanent hair dye product and a second composition that includes an oxidant.

In still another aspect, the present invention provides a method of dyeing hair using the oxidative permanent hair dye product.

Other aspects and preferred embodiments of the invention are discussed infra.

BRIEF DESCRIPTION OF THE DRAWINGS

The above and other features of the present invention will now be described in detail with reference to certain exemplary embodiments thereof illustrated the accompanying drawings which are given hereinbelow by way of illustration only, and thus are not limitative of the present invention, and wherein.

It should be understood that the appended drawings are not necessarily to scale, presenting a somewhat simplified representation of various preferred features illustrative of the basic principles of the invention. The specific design features of the present invention as disclosed herein, including, for example, specific dimensions, orientations, locations, and shapes, will be determined in part by the particular intended application and use environment.

In the figures, reference numbers refer to the same or equivalent parts of the present invention throughout the several figures of the drawing.

DETAILED DESCRIPTION

Hereinafter reference will now be made in detail to various embodiments of the present invention, examples of which are illustrated in the accompanying drawings and described below. While the invention will be described in conjunction with exemplary embodiments, it will be understood that present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the appended claims.

According to an embodiment of the present invention, there is provided a first composition of an oxidative permanent hair dye product that includes a $C_1$-$C_4$ alcohol, an anionic surfactant, a nonionic surfactant, an antioxidant, an oxidative dye, a $C_{14}$-$C_{22}$ fatty alcohol, a metal sequestering agent, an alkali agent, and purified water.

Foam is a type of colloid in which gas is dispersed in a liquid, and stability of the foam depends upon the presence of at least one or more additives, surface tension, and gravity in the same manner as in an emulsion.

Methods of generating foams are classified into methods of precipitating gas dissolved in a liquid and methods of blowing gas into a liquid. According to the former methods, foams are generated by reducing the solubility of gas by heating or reducing pressure, and these methods are applied to beer or aerosol-type products. According to the latter methods, foams are generated by using a manual pump dispenser and the methods are applied to non-aerosol-type products.

Foams generated in a liquid rise up due to density difference. A liquid film of foams floating on the surface of the liquid is thick for a predetermined period of time after being generated, but becomes thinner since liquid flows down with time due to the gravity, so that the foams burst.

In general, in order to produce foams that are rich and last long, a surfactant may be added as an additive to reduce surface tension of a solution or a thickening agent may be added to improve viscosity.

Figure 1:
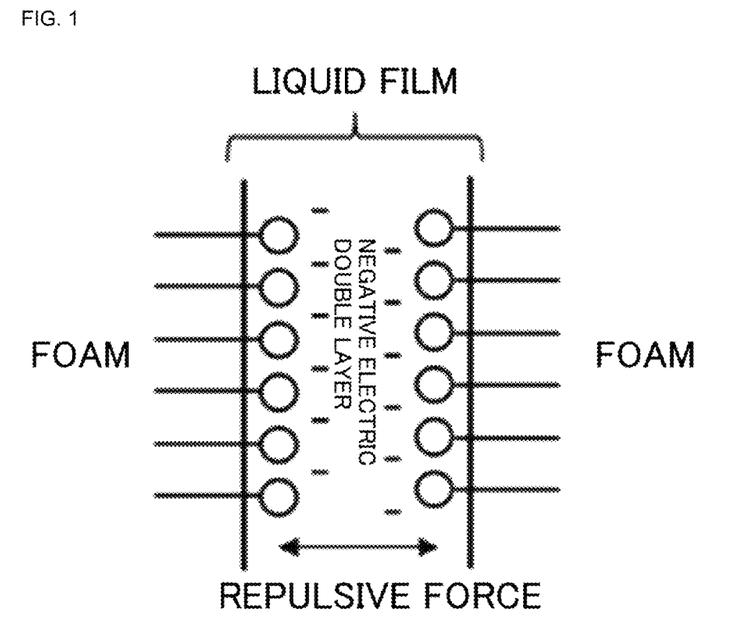
FIG. 1 shows a negative electric double layer and a repulsive force formed in a liquid film by an anionic surfactant.
Figure 2:
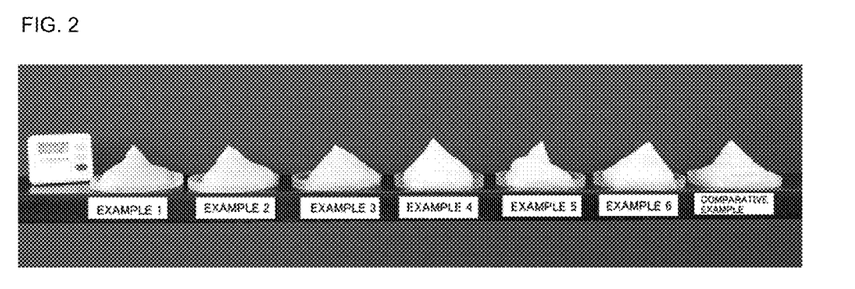
FIG. 2 is a photograph of illustrating foams prepared in Examples 1 to 6 and Comparative Example right after being ejected according to Experimental Example 3.
Figure 3:
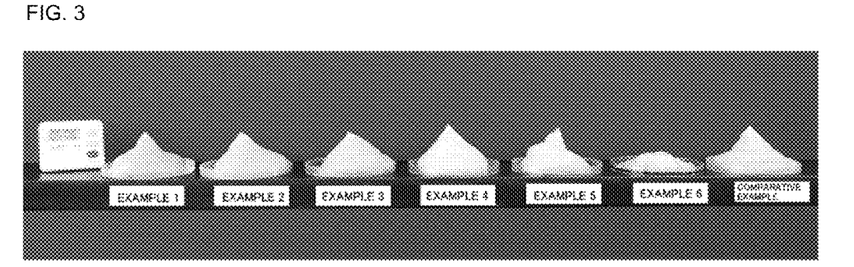
FIG. 3 is a photograph of illustrating foams prepared in Examples 1 to 6 and Comparative Example at 5 minutes after being ejected according to Experimental Example 3.
Figure 4:
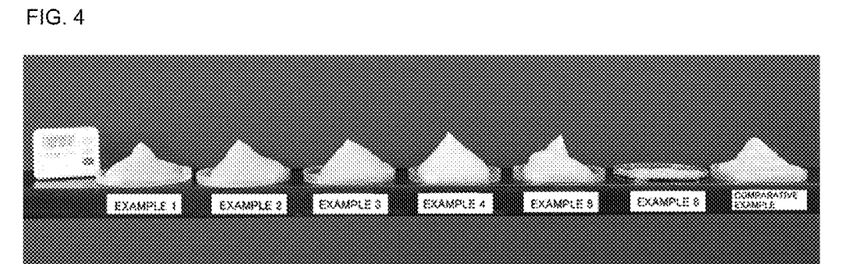
FIG. 4 is a photograph of illustrating foams prepared in Examples 1 to 6 and Comparative Example at 10 minutes after being ejected according to Experimental Example 3.
Figure 5:
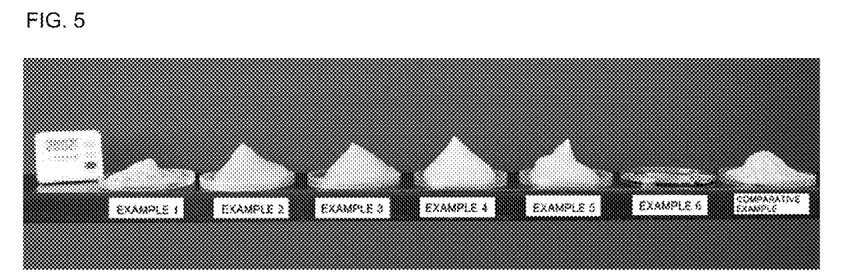
FIG. 5 is a photograph of illustrating foams prepared in Examples 1 to 6 and Comparative Example at 20 minutes after being ejected according to Experimental Example 3.
Figure 6:
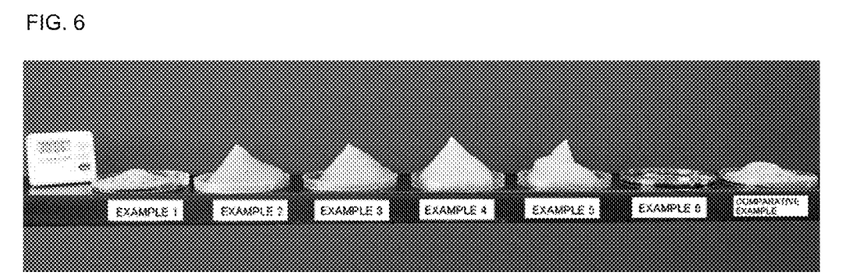
FIG. 6 is a photograph of illustrating foams prepared in Examples 1 to 6 and Comparative Example at 30 minutes after being ejected according to Experimental Example 3.
Figure 7:
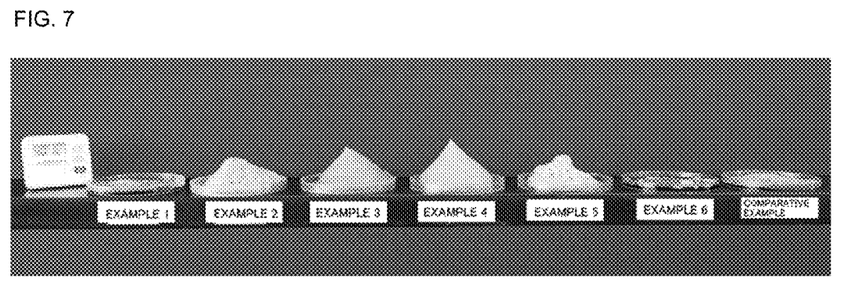
FIG. 7 is a photograph of illustrating foams prepared in Examples 1 to 6 and Comparative Example at 40 minutes after being ejected according to Experimental Example 3.
Figure 8:
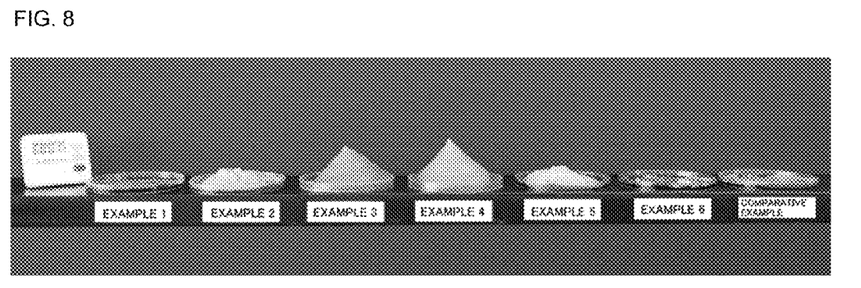
FIG. 8 is a photograph of illustrating foams prepared in Examples 1 to 6 and Comparative Example at 60 minutes after being ejected according to Experimental Example 3.

The surfactant reduces the surface tension between gas and liquid to facilitate the generation of foams and forms an absorption film on the liquid film of the foams to increase lifespan of the foams. Particularly, an anionic surfactant forms a pair of negative electric double layers in the liquid film. The thickness of the liquid film is not reduced less than a predetermined level due to a repulsive power between the two layers, so that foams can be retained for a long period of time. FIG. 1 shows a negative electric double layer and a repulsive force formed in a liquid film by an anionic surfactant.

The stability of foam depends upon an interaction between the foam and an interface between foams. The foam bursts as the liquid film becomes thinner since liquid in the liquid film flows down due to the gravity and liquid flows due to curvature difference of the foam. If the thickness of the liquid film is in the range of about 5 to 15 nm, the liquid film cannot resist the pressure from the inside to burst.

In order to improve the stability of the liquid film constituting the foam, a method of adding an ionic surfactant as an additive, a method of maintaining a thick liquid film by increasing viscosity of liquid of the liquid film by using an aqueous polymer in consideration of characteristics of the liquid film depending on hydration, and a method of stabilizing the hydrated structure of the liquid film by using an aqueous alkali metal such as salt are widely known in the art. However, the gravity has not been considered as a factor of affecting the stability of the foam to improve the stability of the foam by increasing interactions of the interface of foams.

Thus, according to the present invention, a method of improving the stability of the foam by using an additive including an anionic surfactant capable of reducing specific gravity and surface tension of a foam solution is provided.

The additive may be a $C_1$-$C_4$ lower alcohol. Particularly, the additive may include at least one selected from the group consisting of ethyl alcohol, isopropyl alcohol, and n-butyl alcohol having a specific gravity (d20) in the range of 0.785 to 0.816.

In general, foam generated in an aqueous solution such as alcohol has no repulsive force of an electric double layer in a liquid film, has low stability by hydration, and low resistance against thinning of the liquid film due to flowing down of liquid or flow of liquid by curvature difference. Thus, the liquid film easily breaks, so that the foam bursts. However, if the lower alcohol having a function of reducing the surface tension of an aqueous solution and the anionic surfactant are mixed in an appropriate ratio, the generation of foams is accelerated as the surface tension of the aqueous solution decreases, the thickness of the liquid film is not reduced less than a predetermined level, and the flowing down of liquid due to the gravity is delayed as the specific gravity of the liquid film is reduced. Thus, the present inventors have discovered an ideal foam composition.

The content of the $C_1$-$C_4$ lower alcohol may be in the range of 10.0 to 25.0 wt % of the first composition of the oxidative permanent hair dye product. If the content of the $C_1$-$C_4$ lower alcohol is greater than 25.0 wt %, the foam may burst due to too low surface tension. On the other hand, if the content of the $C_1$-$C_4$ lower alcohol is less than 10 wt %, the effect of the lower alcohol is negligible. Preferably, the content of the $C_1$-$C_4$ lower alcohol may be in the range of 15 to 20 wt %.

As the anionic surfactant in the first composition of the oxidative permanent hair dye product, a surfactant in the form of an alkali metal salt or ammonium salt including a $C_{12}$-$C_{16}$ carbon chain may be used. The anionic surfactant may include at least one selected from the group consisting of sodium lauryl sulfate, potassium lauryl sulfate, ammonium lauryl sulfate, sodium myristyl sulfate, sodium cetyl sulfate, sodium cocoyl glutamate, sodium laureth sulfate, and ammonium laureth sulfate. The content of the anionic surfactant may be in the range of 0.5 to 20.0 wt % of the first composition of an oxidative permanent hair dye product.

The nonionic surfactant may be any nonionic surfactant commonly used in a first composition of an oxidative permanent hair dye product. The nonionic surfactant may include at least one selected from the group consisting of ($C_8$-$C_{16}$ alkyl) glucosides, polyoxy($C_1$-$C_6$ alkylene)lanolinalcohols, and polyoxy($C_1$-$C_6$ alkylene)($C_{10}$-$C_{30}$ alkyl)ethers. The nonionic surfactant used herein may include at least one selected from the group consisting of coco-glucoside, polyoxyethylene (POE) lanolin alcohol, POE lauryl ether, POE cetyl ether, POE strearyl ether, POE oleyl ether, and POE behenyl ether. The content of the nonionic surfactant may be in the range of 5.0 to 25.0 wt % of the first composition of an oxidative permanent hair dye product.

The oxidative dye may be any oxidative dye commonly used in an oxidative permanent hair dye product. The oxidative dye may include at least one compound selected from the group consisting of phenylene diamines, pyridine diamines, phenols, naphthols, aminophenols, hydroxyphenols, phenylmethylpyrazolone, pychramic acid or salts thereof, and the like. Particularly, the oxidative dye may include at least one selected from the group consisting of o-phenylenediamine or hydrochlorides or sulfates thereof, m-phenylenediamine or hydrochlorides or sulfates thereof, p-phenylenediamine or hydrochlorides or sulfates thereof, N,N-bis(2-hydroxyethyl)-p-phenylenediamine or hydrochlorides or sulfates thereof, 2,4-diaminophenoxyethanol or hydrochlorides or sulfates thereof, 2-nitro-p-phenylenediamine or hydrochlorides or sulfates thereof, toluene-2,5-diamine or hydrochlorides or sulfates thereof, 2,6-diaminopyridine or hydrochlorides or sulfates thereof, o-aminophenol or hydrochlorides or sulfates thereof, m-aminophenol or hydrochlorides or sulfates thereof, p-aminophenol or hydrochlorides or sulfates thereof, 2-amino-5-nitrophenol, 4-amino-2-hydroxytoluene or hydrochlorides or sulfates thereof, 1-naphthol, resorcinol, phenyl methyl pyrazolone, and picramic acid. The content of the oxidative dye may be in the range of 0.1 to 8.0 wt % based on the first composition of an oxidative permanent hair dye product.

The antioxidant may be any antioxidant commonly used in an oxidative permanent hair dye product. The antioxidant used herein may include at least one selected from the group consisting of sodium sulfite, sodium ascorbate, thioglycolic acid, ammonium thioglycolate, ascorbic acid, and erythorbic acid. The content of the antioxidant may be in the range of 0.1 to 1.0 wt % based on the first composition pf an oxidative permanent hair dye product.

The fatty alcohol may be a $C_{14}$-$C_{22}$ saturated or unsaturated fatty alcohol. The fatty alcohol used herein may include at least one selected from the group consisting of myristyl alcohol, cetyl alcohol, stearyl alcohol, oleyl alcohol, and behenyl alcohol. The content of the fatty alcohol may be in the range of 0.1 to 5.0 wt % of the first composition including an oxidative permanent hair dye.

The metal sequestering agent may be ethylenediaminetetraacetic acid (EDTA) or salts thereof, particularly, disodium EDTA. The content of the metal sequestering agent may be in the range of 0.05 to 0.4 wt % of the first composition including an oxidative permanent hair dye.

The alkali agent may include at least one selected from the group consisting of ammonia, ammonium carbonate, ammonium bicarbonate, mono($C_1$-$C_6$ alcohol)amines, di($C_1$-$C_6$ alcohol)amines, and tri($C_1$-$C_6$ alcohol)amines. The alkali agent used herein may include at least one selected from the group consisting of ammonia water, ammonium bicarbonate, monoethanolamine, and triethanolamine. The content of the alkali agent may be in the range of 1.0 to 15.0 wt % of the first composition of an oxidative permanent hair dye product.

The content of purified water may be in the range of 0.6 to 82.25 wt % based on the first composition of an oxidative permanent hair dye product.

According to another embodiment of the present invention, there is provided an oxidative permanent hair dye product including the first composition of an oxidative permanent hair dye product and a second composition including an oxidant.

The weight ratio of the first composition and the second composition may be in the range of 20 to 60:40 to 80.

The second composition may include an oxidant, a stabilizer, an anionic surfactant, a pH regulator, a $C_{14}$-$C_{22}$ fatty alcohol, and purified water.

The oxidant in the second composition may be any oxidant commonly used in oxidative permanent hair dye products. The oxidant used herein may include at least one selected from the group consisting of hydrogen peroxide solution, sodium percarbonate, and sodium perborate. The content of the oxidant may be in the range of 5 to 30 wt % of the second composition including an oxidant.

The stabilizer in the second composition may be any oxidant commonly used in oxidative permanent hair dye products. The stabilizer used herein may include at least one selected from the group consisting of sodium stannate, acetanilide, and phenacetin. The content of the stabilizer may be in the range of 0.01 to 1 wt % of the second composition.

In addition, as the anionic surfactant in the second composition, a surfactant in the form of an alkali metal salt or ammonium salt including a $C_{12}$-$C_{16}$ carbon chain may be used. The anionic surfactant may include at least one selected from the group consisting of sodium lauryl sulfate, potassium lauryl sulfate, ammonium lauryl sulfate, sodium myristyl sulfate, sodium cetyl sulfate, sodium cocoyl glutamate, sodium laureth sulfate, and ammonium laureth sulfate. The content of the anionic surfactant may be in the range of 1 to 20 wt % of the second composition.

In the second composition including an oxidant, the pH regulator may include at least one selected from the group consisting of phosphoric acid and tetra sodium pyrophosphate. The content of the pH regulator may be in the range of 0.01 to 1 wt % of the second composition.

In the second composition including an oxidant, the $C_{14}$-$C_{22}$ fatty alcohol may include at least one selected from the group consisting of myristyl alcohol, cetyl alcohol, stearyl alcohol, and behenyl alcohol. The content of the fatty alcohol may be in the range of 0.1 to 5 wt % of the second composition.

The content of purified water may be in the range of 50 to 80 wt % of the second composition.

According to another embodiment of the present invention, there is provided a method of dyeing hair, the method including: preparing an oxidative permanent hair dye product by generating foams by mixing the first composition and the second composition; applying the foams of the oxidative permanent hair dye product to hair; and leave on for 5 to 30 minutes.

The hair to which the dye product is applied may be leave on for 5 to 20 minutes for a quick dye.

EXAMPLES

The following examples illustrate the invention and are not intended to limit the same.

Example 1

A liquid phase first composition of an oxidative permanent hair dye product was prepared by mixing an oxidative hair dye including 3.0 wt % of p-phenylenediamine, 1.0 wt % of p-aminophenol, 0.2 wt % of 4-amino-2-hydroxytoluene, and 1.0 wt % of resorcinol, 0.5 wt % of sodium sulfite as an antioxidant, 0.2 wt % of disodium EDTA as a metal sequestering agent, an anionic surfactant including 6.0 wt % of sodium laureth sulfate and 4.0 wt % of sodium cocoyl glutamate, a nonionic surfactant including 5.0 wt % of coco-glucoside and 3.0 wt % of POE lauryl ether, 3.5 wt % of myristyl alcohol as a fatty alcohol, and 61.6 wt % of purified water, heating the mixture at 75 to 85° C. to dissolve the ingredients, cooling the mixture to 40 to 45° C., adding 5.0 wt % of ethyl alcohol as a $C_1$-$C_4$ lower alcohol and an alkali agent including 4.0 wt % of ammonia water, and 2.0 wt % of monoethanolamine to the mixture, stirring the mixture.

A liquid phase second composition of the oxidative permanent hair dye product was prepared by mixing 10.0 wt % of sodium lauryl sulfate as a anionic surfactant, 1.5 wt % of cetyl alcohol as a fatty alcohol, 0.1 wt % of sodium stannate as a stabilizer, a pH regulator including 0.1 wt % of phosphoric acid and 0.05 wt % of tetra sodium pyrophosphate, and 71.25 wt % of purified water, heating the mixture at 75 to 85° C. to dissolve the ingredients, cooling the mixture to 40 to 45° C., adding 17.0 wt % of a hydrogen peroxide solution (35 wt % concentration) as an oxidant to the mixture, and stirring the mixture.

Example 2

The first and second compositions were prepared in the same manner as in Example 1, except that 10.0 wt % of ethyl alcohol and 56.6 wt % of purified water were used in the first composition.

Example 3

The first and second compositions were prepared in the same manner as in Example 1, except that 15.0 wt % of ethyl alcohol and 51.6 wt % of purified water were used in the first composition.

Example 4

The first and second compositions were prepared in the same manner as in Example 1, except that 20.0 wt % of ethyl alcohol and 46.6 wt % of purified water were used in the first composition.

Example 5

The first and second compositions were prepared in the same manner as in Example 1, except that 25.0 wt % of ethyl alcohol and 41.6 wt % of purified water were used in the first composition.

Example 6

The first and second compositions were prepared in the same manner as in Example 1, except that 30.0 wt % of ethyl alcohol and 36.6 wt % of purified water were used in the first composition.

Comparative Example

The first and second compositions were prepared in the same manner as in Example 1, except that ethyl alcohol was not used and 66.6 wt % of purified water was used in the first composition. Contents of the ingredients of the first and second compositions of the hair dye products prepared in Examples 1 to 6 and Comparative Example are shown in Table 1 below.

TABLE 1

| (wt %) | Ex. 1 | Ex. 2 | Ex. 3 | Ex. 4 | Ex. 5 | Ex. 6 | Comp. Ex. |
|---|---|---|---|---|---|---|---|
| first composition | | | | | | | |
| p-phenylenediamine | 3.00 | 3.00 | 3.00 | 3.00 | 3.00 | 3.00 | 3.00 |
| p-aminophenol | 1.00 | 1.00 | 1.00 | 1.00 | 1.00 | 1.00 | 1.00 |
| 4-amino-2-hydroxytoluene | 0.20 | 0.20 | 0.20 | 0.20 | 0.20 | 0.20 | 0.20 |
| resorcinol | 1.00 | 1.00 | 1.00 | 1.00 | 1.00 | 1.00 | 1.00 |
| sodium sulfite | 0.50 | 0.50 | 0.50 | 0.50 | 0.50 | 0.50 | 0.50 |
| disodium EDTA | 0.20 | 0.20 | 0.20 | 0.20 | 0.20 | 0.20 | 0.20 |
| sodium laureth sulfate | 6.00 | 6.00 | 6.00 | 6.00 | 6.00 | 6.00 | 6.00 |
| sodium cocoyl glutamate | 4.00 | 4.00 | 4.00 | 4.00 | 4.00 | 4.00 | 4.00 |
| alkyl(8-16)glucoside | 5.00 | 5.00 | 5.00 | 5.00 | 5.00 | 5.00 | 5.00 |
| POE(23) lauryl ether | 3.00 | 3.00 | 3.00 | 3.00 | 3.00 | 3.00 | 3.00 |
| myristyl alcohol | 3.50 | 3.50 | 3.50 | 3.50 | 3.50 | 3.50 | 3.50 |
| ethyl alcohol | 5.00 | 10.00 | 15.00 | 20.00 | 25.00 | 30.00 | — |
| ammonia water | 4.00 | 4.00 | 4.00 | 4.00 | 4.00 | 4.00 | 4.00 |
| monoethanolamine | 2.00 | 2.00 | 2.00 | 2.00 | 2.00 | 2.00 | 2.00 |
| purified water | 61.60 | 56.60 | 51.60 | 46.60 | 41.60 | 36.60 | 66.60 |
| second composition | | | | | | | |
| sodium lauryl sulfate | 10.00 | 10.00 | 10.00 | 10.00 | 10.00 | 10.00 | 10.00 |
| cetyl alcohol | 1.50 | 1.50 | 1.50 | 1.50 | 1.50 | 1.50 | 1.50 |
| sodium stannate | 0.10 | 0.10 | 0.10 | 0.10 | 0.10 | 0.10 | 0.10 |
| phosphoric acid | 0.10 | 0.10 | 0.10 | 0.10 | 0.10 | 0.10 | 0.10 |
| tetra sodium pyrophosphate | 0.05 | 0.05 | 0.05 | 0.05 | 0.05 | 0.05 | 0.05 |

TABLE 1-continued

| (wt %) | Ex. 1 | Ex. 2 | Ex. 3 | Ex. 4 | Ex. 5 | Ex. 6 | Comp. Ex. |
|---|---|---|---|---|---|---|---|
| hydrogen peroxide solution (35 wt % concentration) | 17.00 | 17.00 | 17.00 | 17.00 | 17.00 | 17.00 | 17.00 |
| purified water | 71.25 | 71.25 | 71.25 | 71.25 | 71.25 | 71.25 | 71.25 |

Experimental Example 1

Evaluation of Transparency of First Composition According to Long-Term Storage

In order to evaluate effect of ethyl alcohol, as a lower alcohol, on long-term storage stability of the first composition, the first compositions prepared in Examples 1 to 6 and Comparative Example were stored at −5° C. for 30 days, and transparency of the first compositions was evaluated as follows. The results are shown in Table 2 below.

★★★: transparent at −5° C. for 30 days
★★☆: turbid in the early stage, and transparent after being left at room temperature (24° C.) for 24 hours
★☆☆: turbid in the early stage, and semi-transparent after being left at room temperature (24° C.) for 24 hours, but not precipitated
☆☆☆: turbid in the early stage, and precipitated after being left at room temperature (24° C.) for 24 hours Experimental Example 2

Evaluation of Foam Generative Ability

The first composition and the second composition of the hair dye products prepared in Examples 1 to 6 and Comparative Example were respectively mixed in the weight ratio of 30:50, and fineness of foams generated by using a non-aerosol-type foam generating dispenser was observed. The results are shown in Table 2 below. As shown in Table 2, if foams of a liquid oxidative permanent hair dye product including an anionic surfactant are generated by using a foam generating dispenser, it was identified that the foam generative ability of a composition including ethyl alcohol as a lower alcohol was better than that of a composition not including ethyl alcohol.

★★★: fine and uniform foam
★★☆: uniform foam
★☆☆: non-uniform foam
☆☆☆: no foam

Experimental Example 3

Evaluation of Foam Retention Ability

The first composition and the second composition prepared in Examples 1 to 6 and Comparative Example were respectively mixed in a ratio of 30:50, and it was observed whether foams generated by using a non-aerosol-type foam generating dispenser were continuously retained without disappearing for 1 hour at room temperature. The results are shown in Table 2 below. As shown in Table 2, it was identified that foams were continuously retained for more than 30 minutes without disappearing when the content of ethyl alcohol, as a lower alcohol, was in the range of 10.0 to 25.0 wt %. FIGS. 2 to 8 show photographs of foams right after being ejected and at 5, 10, 20, 30, 40, and 60 minutes after being ejected.

★★★: Foams are continuously retained for 60 minutes without disappearing.
★★☆: Foams are continuously retained for 30 minutes without disappearing.
★☆☆: Foams are continuously retained for 10 minutes without disappearing.
☆☆☆: Foams are not continuously retained for more than 10 minutes.

Experimental Example 4

Measuring Surface Tension

Surface tension the compositions prepared in Examples 1 to 6 and Comparative Example was measured according to the concentration of ethyl alcohol, as a lower alcohol. The surface tension was measured using a surface tension measurer (Model No.: Easy Dyne, manufactured by Kruss, Germany). The results are shown in Table 2 below. As a result of measuring the surface tension, it was identified that as the concentration of ethyl alcohol increases in the composition, the surface tension decreases. While the surface tension rapidly decreases until the concentration of ethyl alcohol in the early stage reached about 25%, the surface tension gradually decreases thereafter. Based on the results of Experimental Example 3, it was identified that the stability of foams was maximized when the surface tension was in the range of 40.0 to 50.0 nN/m.

Experimental Example 5

Measurement of Specific Gravity

Specific gravity of the compositions prepared in Examples 1 to 6 and Comparative Example was measured in order to observe effect of the gravity on the liquid film of foams according to the concentration of ethyl alcohol as a lower alcohol. The specific gravity was measured by using a specific gravity hydrometer at 20° C. The results are shown in Table 2 below. As shown in Table 2, it was identified that the specific gravity of the composition decreases as the concentration of ethyl alcohol as a lower alcohol increases.

Experimental Example 6

Evaluation of Hair Dyeing Ability

In order to evaluate hair dyeing ability, first compositions of the hair dye products prepared in Examples 1 to 6 and Comparative Example were applied to white hair having a weight of 1.0 g and a length of 8.0 cm, and leave on the hair for 20 minutes. Then, the hair was washed under running water for 2 minutes and dried, and then hair dyeing ability of the products was observed. The hair dyeing ability was evaluated by using a colorimeter (Model No.: Spectrophotometer CM-508C, manufactured by MINOLTA CO. LTD., JAPAN). Brightness (L*) of each sample was measured based on a reference value of a standard white hair. L* indicates brightness, and as L* increases, brightness of color increases. The results of the evaluation are shown in Table 2 below. As shown in Table 2, it was identified that hair was uniformly dyed by using the compositions of Examples 1 to 6 and Comparative Example. It can be seen that low alcohol does not influence the hair dyeing ability of the liquid phase oxidative hair dye product.

TABLE 2

| class | Ex. 1 | Ex. 2 | Ex. 3 | Ex. 4 | Ex. 5 | Ex. 6 | Comp. Ex. |
|---|---|---|---|---|---|---|---|
| transparency of first composition | ★★★ | ★★★ | ★★★ | ★★★ | ★★☆ | ★☆☆ | ★★★ |
| foam generative force | ★★★ | ★★★ | ★★★ | ★★★ | ★★★ | ★★★ | ★★☆ |
| foam retention force | ★☆☆ | ★★☆ | ★★★ | ★★★ | ★★☆ | ☆☆☆ | ★☆☆ |
| surface tension (nN/m) | 56.48 | 50.88 | 46.80 | 42.56 | 40.98 | 38.00 | 61.04 |
| specific gravity ($d_{20}$) | 0.992 | 0.985 | 0.978 | 0.970 | 0.962 | 0.955 | 1.024 |
| hair dyeing force (L*) | 18.60 | 19.96 | 19.23 | 18.53 | 19.02 | 19.22 | 19.38 |

According to the oxidative permanent hair dye product according to the present invention, foams generated by mixing a liquid first composition that includes a dye and a liquid second composition that includes an oxidant are continuously retained on hair for more than 30 minutes, and thus hair, even close to the root, can be simply and conveniently colored in the same manner as shampooing without using a comb or brush.

In addition, problems of spots caused by time difference of the application of conventional hair dye products due to long time for application of about 5 to 30 minutes can be prevented by reducing time taken for applying the foamed hair dye product to hair less than 3 minutes.

The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

What is claimed is:

1. A first composition of an oxidative permanent hair dye product comprising:
   a $C_1$-$C_4$ alcohol,
   an anionic surfactant that is an alkali metal salt or ammonium salt comprising a $C_{12}$-$C_{16}$ carbon chain,
   a nonionic surfactant that comprises at least one selected from the group consisting of ($C_8$-$C_{16}$ alkyl)glucosides, polyoxy($C_1$-$C_6$ alkylene)lanolinalcohols, and polyoxy($C_1$-$C_6$ alkylene)($C_{10}$-$C_{30}$ alkyl)ethers,
   an antioxidant,
   an oxidative dye that comprises at least one selected from the group consisting of phenylene diamines, pyridine diamines, phenols, naphthols, aminophenols, hydroxyphenols, phenylmethylpyrazolone, pychramic acid or salts thereof,
   a $C_{14}$-$C_{22}$ fatty alcohol,
   a metal sequestering agent,
   an alkali agent, and
   purified water, and a second composition that comprises an oxidant, a stabilizer, an anionic surfactant, a pH regulator, and a $C_{14}$-$C_{22}$ fatty alcohol.

2. The first composition of claim 1, wherein the first composition comprises 10.0 to 25.0 wt % of a $C_1$-$C_4$ alcohol, 0.5 to 20.0 wt % of an anionic surfactant, 5.0 to 25.0 wt % of a nonionic surfactant, 0.1 to 1.0 wt % of an antioxidant, 0.1 to 8.0 wt % of an oxidative dye, 1.0 to 5.0 wt % of a $C_{14}$-$C_{22}$ fatty alcohol, 0.05 to 0.4 wt % of a metal sequestering agent, 1.0 to 15.0 wt % of an alkali agent, and 0.6 to 82.25 wt % of purified water.

3. The first composition of claim 1, wherein the $C_1$-$C_4$ alcohol comprises at least one selected from the group consisting of ethyl alcohol, isopropyl alcohol, and n-butyl alcohol.

4. The first composition of claim 1, wherein the anionic surfactant comprises at least one selected from the group consisting of sodium lauryl sulfate, potassium lauryl sulfate, ammonium lauryl sulfate, sodium myristyl sulfate, sodium cetyl sulfate, sodium cocoyl glutamate, sodium laureth sulfate, and ammonium laureth sulfate.

5. The first composition of claim 1, wherein the nonionic surfactant comprises at least one selected from the group consisting of coco-glucoside, polyoxyethylene (POE) lanolin alcohol, POE lauryl ether, POE cetyl ether, POE strearyl ether, POE oleyl ether, and POE behenyl ether.

6. The first composition of claim 1, wherein the antioxidant comprises at least one selected from the group consisting of sodium sulfite, sodium ascorbate, thioglycolic acid, ammonium thioglycolate, ascorbic acid, and erythorbic acid.

7. The first composition of claim 1, wherein the oxidative dye comprises at least one selected from the group consisting of o-phenylenediamine or hydrochlorides or sulfates thereof, m-phenyleriediamine or hydrochlorides or sulfates thereof, p-phenylenediamine or hydrochlorides or sulfates thereof, N,N-bis(2-hydroxyethyl)-p-phenylenediamine or hydrochlorides or sulfates thereof, 2,4-diaminophenoxyethanol or hydrochlorides or sulfates thereof, 2-nitro-p-phenylenediamine or hydrochlorides or sulfates thereof, toluene-2,5-diamine or hydrochlorides or sulfates thereof, 2,6-diaminopyridine or hydrochlorides or sulfates thereof, o-aminophenol or hydrochlorides or sulfates thereof, m-aminophenol or hydrochlorides or sulfates thereof, p-aminophenol or hydrochlorides or sulfates thereof, 2-amino-5-nitrophenol, 4-amino-2-hydroxytoluene or hydrochlorides or sulfates thereof, 1-naphthol, resorcinol, phenyl methylpyrazolone, and picramic acid.

8. The first composition of claim 1, wherein the fatty alcohol comprises at least one selected from the group consisting of myristyl alcohol, cetyl alcohol, stearyl alcohol, oleyl alcohol, and behenyl alcohol.

9. The first composition of claim 1, wherein the metal sequestering agent is ethylenediaminetetraacetic acid (EDTA) or salts thereof.

10. The first composition of claim 1, wherein the alkali agent comprises at least one selected from the group consisting of ammonia, ammonium carbonate, ammonium bicarbonate, mono($C_1$-$C_6$ alcohol)amines, di($C_1$-$C_6$ alcohol)amines, and tri($C_1$-$C_6$ alcohol)amines.

11. The oxidative permanent hair dye product of claim 1, wherein the weight ratio of the first composition and the second composition is in the range of 20 to 60:40 to 80.

12. The oxidative permanent hair dye product of claim 1, wherein the second composition comprises 5 to 30 wt % of the oxidant, 0.01 to 1 wt % of the stabilizer, 1 to 20 wt % of the anionic surfactant, 0.01 to 1 wt % of the pH regulator, 0.1 to 5 wt % of the fatty alcohol, and 50 to 80 wt % of purified water.

13. The oxidative permanent hair dye product of claim 1, wherein the second composition comprises at least one oxidant selected from the group consisting of hydrogen peroxide solution, sodium percarbonate, and sodium perborate,
- at least one stabilizer selected from the group consisting of sodium stannate, acetanilide, and phenacetin,
- an anionic surfactant in the form of an alkali metal salt or ammonium salt comprising a $C_{12}$-$C_{16}$ chain,
- at least one pH regulator selected from the group consisting of phosphoric acid and tetra sodium pyrophosphate, and
- a $C_{14}$-$C_{22}$ fatty alcohol.

14. A method of dyeing hair, the method comprising:
- preparing an oxidative permanent hair dye product by generating foams by mixing the first composition and the second composition of claim 1;
- applying the foams of the oxidative permanent hair dye product to hair; and
- leave on for 5 to 30 minutes.

* * * * *